United States Patent [19]

Kamarei et al.

[11] Patent Number: 4,776,173
[45] Date of Patent: Oct. 11, 1988

[54] METHOD FOR EXTRACTING A SUBSTANCE FROM ANIMAL DERIVED MATERIAL

[75] Inventors: Ahmad R. Kamarei, Arlington, Mass.; Robert Sinn, New York, N.Y.

[73] Assignee: Angio-Medical Corporation, New York, N.Y.

[21] Appl. No.: 148,127

[22] Filed: Jan. 26, 1988

Related U.S. Application Data

[63] Continuation of Ser. No. 811,507, Dec. 20, 1985, abandoned.

[51] Int. Cl.⁴ .............................................. F25D 13/06
[52] U.S. Cl. .......................................... 62/63; 62/320; 241/23; 241/65; 241/DIG. 37
[58] Field of Search ............... 62/63, 78, 320; 241/14, 241/23, 65, DIG. 37

[56] References Cited

U.S. PATENT DOCUMENTS

| | | | |
|---|---|---|---|
| 637,465 | 11/1899 | Hutchinson | 241/23 |
| 2,575,341 | 11/1951 | Gollmar | 62/17 |
| 3,771,729 | 11/1973 | Frable | 241/65 |
| 4,023,734 | 5/1977 | Hervé et al. | 241/17 |
| 4,273,294 | 6/1981 | Hollely et al. | 241/18 |
| 4,406,700 | 9/1983 | Maeland | 75/251 |
| 4,483,488 | 11/1984 | Luff et al. | 241/23 |
| 4,509,695 | 4/1985 | Bessman | 241/2 |

OTHER PUBLICATIONS

Melton, S: Food Technology, Jul. 1983, pp. 105–111 and 116.
Gardner, J: Agric. Good Chem 27(2): 220–229 (1979).
Logani et al., Lipids 15(6): 485–495 (1980).
Gray, J., J. Am. Oil. Chem. Soc. 55: 539–546 (1978).
Perkins, Ed., *Analysis of Lipids and Lipoproteins* (American Oil Chemists' Society, 1975), pp. 1–22.
"Cryogenic Grinding Systems" (Liquid Carbonics Brochure), 1985.
"Model LNP-15 FM Cryogenic Grinding Precooling System" (Liquid Carbonics Brochure) Nov. 1984.

*Primary Examiner*—Ronald C. Capossela
*Attorney, Agent, or Firm*—Felfe & Lynch

[57] ABSTRACT

Animal or plant derived materials are prepared for extraction of desired substances therefrom by grinding said materials at or below their Brittleness Temperature. This treatment allows fracture of the materials into small particles with high surface area to volume, as well as high volume to mass ratios, and disrupts membranes of tissues, organs, cells or organelles which would otherwise prevent or limit separation of desired biomolecules.

22 Claims, 1 Drawing Sheet

Fig. 1.

METHOD FOR EXTRACTING A SUBSTANCE FROM ANIMAL DERIVED MATERIAL

This application is a continuation of application Ser. No. 811,507, filed Dec. 20, 1985, now abandoned.

BACKGROUND

In separation processes (e.g., extraction, leaching, drying, freeze, drying, etc.) where mass and/or a combination of mass and heat transfer are involved, the physical form of feed, i.e., the particle size and the attendant ratio of surface area to volume and volume to mass (specific volume) usually has a great impact on the efficiency of the process. This efficiency can be expressed in terms of using less solvent or energy, faster processing rate, higher percent recovery, and in many cases, higher quality of the final products. For example, in leaching by organic solvents or supercritical fluids (SCF), the greater the area of the solute exposed to solvent, the more efficient the process is. Likewise, in freeze drying, the heat flux and the rate of sublimation is directly proportional to the subject area of the material under process.

When extracting desired substances from plant and animal materials, such as tissues, cells, and the like, it is important that the particle size of the material being extracted be as small as possible. There are three reasons why small size is important: (1) the action or processes involved in obtaining small particle size break the walls, membranes and structures which physically protect and surround cells, organelles, and extracellular materials; (2) it is necessary in extraction processes to expose as much of the molecular species to be extracted as is possible to the solvent; and (3) in thermal extraction, it is important that molecular species be physically exposed.

Disruption of membranes, and maximum exposure can be obtained by treating plant or animal materials at or below their brittleness temperature. This is defined herein as the temperature below which a frozen material fractures into small particles when stress is applied thereto.

In order to prepare animal or plant derived materials, i.e., tissues, organs, cells and organelles for separation processes such as extraction and leaching via aqueous solvents, organic solvents, SCF, and/or application of thermal energy, the solutes (usually contents of the cells, protoplasm and/or membranes) should become easily available and exposed to the extracting media. This means that the cell membrane should be ruptured. The greater the ratio of surface area to volume of such animal derived solutes, the more efficient the process is.

Due to inherent thermal sensitivity of animal derived material, in preparing of such materials, one should avoid using "heat" over biomolecular breakdown temperature, because it may cause undesirable reactions (e.g., protein denaturation, lipid and carbohydrate breakdown, inactivation of desirable biomolecules) and production of undesirable products (e.g., Maillard Reaction Products, pyrolysis products) which, in turn, may adversely affect the separation process. Consequently, preparation of animal derived materials for separation processes should be done at the minimum possible temperature.

On the other hand, some animal derived materials, due to their inherent rheological behaviors, cannot be homogenized at regular temperatures. For example, adipose tissues and omentum cannot be homogenized (ground) at room temperature, refrigerator temperature, or even higher freezing temperatures. The high plasticity of these tissues is not compatible with grinding processes. In traditional methods, phosphate buffered saline (PBS) or water is added as a "filter" to animal fatty tissues in order to make the homogenization possible. In other words without a medium, the tissue cannot be disintegrated by mere homogenization. Addition of aqueous phase, however, requires its subsequent removal from the system by a time consuming or energy consuming step such as centrifugation or freeze drying.

In conclusion, for preparation of animal and plant derived materials for separation processes, a method is needed which does not require an extra phase or substance, ruptures the cell membranes and walls effectively, increases the exposing surface area of the cell contents to the separating driving force (solvent, SCF, thermal energy, vacuum, etc.), does not involve damaging heat treatment, is compatible with biomolecules, technology adaptable and is economically feasible.

It is an object of this invention to rapidly prepare animal or plant materials for extraction by preparing said materials at temperatures at or below their brittleness temperature in order to enable fracture of said materials into particles with optimum size and attendant ratios of surface area to volume and volume to mass.

It is a further object of the invention to provide an improved method for obtaining desirable substances from animal and plant materials, including but not limited to lipids, carbohydrates, proteins and all other biomolecules which does not effect or has only minimal effect on the structure or reactivity of said biomolecules.

Yet another object of this invention is to extract materials from animal and plant which have been treated at brittleness temperatures or below to obtain desired substances therefrom.

Yet a further object of the invention is to provide a method of separation such as drying, freeze drying, leaching and extraction using aqueous and organic solvents and/or supercritical fluids (SCFs) in connection with materials fractured at or below their brittleness temperatures.

How these and other objects of the invention are accomplished will be seen from the disclosure which follows.

PRIOR ART

While freezing is a recognized technique for preservation of tissues, its use coupled with grinding and/or fracturing at or below the brittleness temperatures to improve follow-up separation, has never before been envisioned.

U.S. Pat. No. 4,141,887 discloses a way of separating materials from plasma. Cryoprecipitates of blood clotting products are obtained without grinding using temperatures below $-22°$ C. The precipitation results from denaturing, and hence changes in three dimensional structure, of the protein molecules.

Other patents employ grinding to prepare tissues for extraction, as is evidenced by, e.g., U.S. Pat. No. 4,296,099 (grinding embryonic calf skin tissue in order to obtain desirable extracts). U.S. Pat. No. 4,349,540 describes grinding procaryotic cells to obtain ribosomal fractions. Again, however, said grinding is not done at brittleness temperatures. U.S. Pat. No. 4,429,969 describes room temperature wet grinding of plant material (date fruit), while U.S. Pat. No. 4,455,298 describes dessication of molluscs, followed by grinding to obtain a desirable lipid extract.

None of these references teach brittleness temperature or fracturing at said temperature and fracturing and/or grinding of animal or plant materials at or below such temperature in order to obtain desired materials therefrom.

DETAILED DESCRIPTION OF PREFERRED EMBODIMENTS

Figure 1:
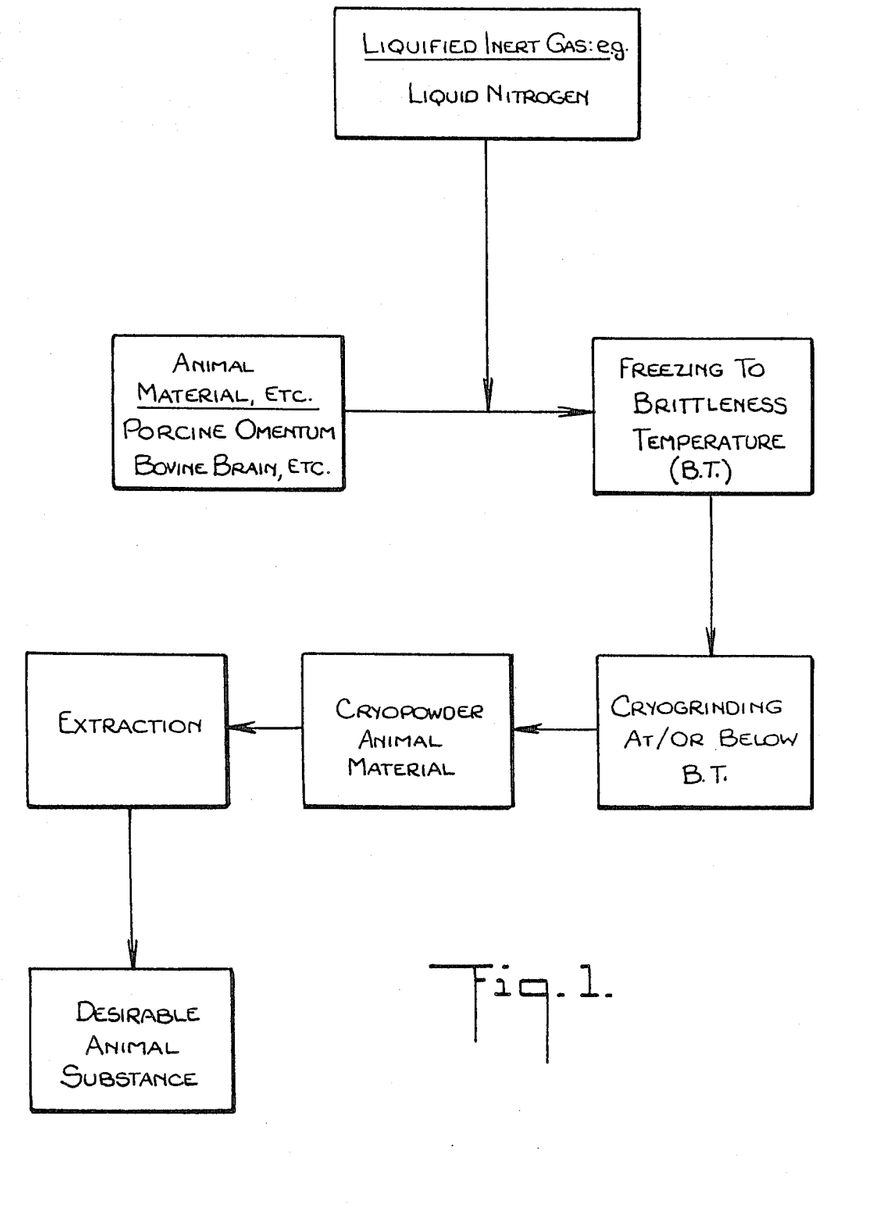
FIG. 1 shows, schematically, the steps of the invention described herein.

I. Grinding at or below Brittleness Temperature of animal or plant derived materials A. Prefreezing treatment:

Upon recovery of animal or plant tissues, organs, or cells, all sanitary practices should be made. For example, they should be chilled promptly to low temperature (0° C.). This treatment prevents or drastically reduces undesirable microbial growth, enzymatic activity, and autolytic chemical reactions.

Just before freezing to brittleness temperature, the larger tissues should be cut into relatively small pieces (e.g., 1-5 grams). This will improve the freezing rate of tissues and facilitate their later handling during the cryogrinding step or steps. Attempts should be made to minimize pretreatment time and tissues should become frozen without undue delay.

B. Freezing treatment:

This step is based on freezing the pieces of the desired tissue and lowering its temperature to an emperically critical "Brittleness Temperature" which converts the unbreakable, viscous, and sticky (e.g. fatty tissue) materials into an extremely brittle and fragile substance. Brittleness temperature depends primarily on the species and composition of the tissue (water, lipids, proteins, carbohydrates, minerals) and therefore its thermal properties. The rate of crystallization (i.e., nucleation and crystal growth) of water will affect the size of crystals. Slow rate of crystallization results in formation of large extracellular water crystals which may cause some rupture of cell membranes, but such effects and even repeated freeze-thaw process have negligible effects in comparison to cell rupture by cryogrinding. It is preferred, however, to keep the physical structure of the tissue cells up to the cryogrinding step, intact. This means that, all other factors being equal, the fastest possible freezing rate should be employed. Associated with freezing process, is the initial volume increase of the tissue. Pure water at 0° C. expands approximately 9% when transformed into ice at the same temperature. Most tissues also expand on freezing but to a lesser extent than pure water.

Freezing can be accomplished via various methods, including:
1. Air Freezing:
   (a) Blast freezing
   (b) Fluidized-bed freezing
2. Plate Freezing
3. Liquid-immersion Freezing
4. Cryogenic Freezing (freezant undergoes a change of state):
   (a) Liquid Nitrogen (LN$_2$), −196° C. (77K)
   (b) Subliming Carbon dioxide (dry ice), −79° C. (194K)
   (c) CCl$_2$F$_2$ (refrigerant −12), −30° C. (243K)

Cryogenic freezing with LN$_2$, among all above methods, is the most desirable method for the following reasons:

Liquid nitrogen is a safe, non-toxic, and non-flammable cryogenic medium which is universally used in food, pharmaceutical, and other industries.

Since the freezing rate is extremely fast, the physical structure of cells is preserved (intracellular small crystals) and there is negligible dehydration loss. Oxygen is also excluded from the boiling freezant. Consequently the freezing damage to the tissue is at the minimum possible extent.

Low capital investment, simple equipment, high production rate in a minimal space, adaptable for continuous flow operation and various product sizes.

The only disadvantage of liquid nitrogen could be its relatively high operating cost.

C. Cryogrinding treatment:

Upon obtaining the brittle pieces of tissues, they may be transferred to any size reduction equipment such as Waring blender and homogenized (ground) for the desired length of time, i.e., a few minutes at 22,000 RPM. At larger scales, roll mills with both attrition and impact grinding could be used. It is important that the tissue be kept at or below its brittle temperature throughout the grinding process. Grinding below the brittleness temperature is required in order to produce the necessary small particle size. For this purpose one could occasionally add, if needed, quantities of LN$_2$ to the size-reduction equipment, provided that there is a vent to allow exhaustion of the nitrogen vapor generated during the process.

Upon completion of the process, an extremely fine, and free-flowing (non-sticky) cryoground tissue ("tissue powder") results. The resultant powder obviously may contain some granular lumps as well as fine indiscrete particles.

Parallel to the tremendous increase of surface area (i.e., ratio of surface area to volume), there is also an inherent reduction of density. As an example, density of omentum powder is 0.44 ($\pm 5\%$) g/ml which is almost half of the density of lipids extracted from omentum.

II. Cryosieving of Tissue Powder

The resultant cryoground tissue powder, while extremely fine, is not "uniform" with regard to size. Consequently, if uniformity in a particular size range is desired for the following steps, tissue powder should be sieved at or below its brittleness temperature. For this purpose, one may use stacked stainless steel standard sieves (Table 1; AOAC, 1984).

TABLE 1

| Nominal Dimensions of Standard Test Sieves (U.S.A. Standard Series) | | | |
|---|---|---|---|
| Sieve Designation | | Nominal | Nominal |
| International Standard[a] (ISO) | U.S.A. Standard | Sieve Opening inches | Wire Diameter mm |
| 12.5 mm[b] | ½ in.[b] | 0.500 | 2.67 |
| 11.2 mm | 7/16 in. | 0.438 | 2.45 |
| 9.5 mm | ⅜ in. | 0.375 | 2.27 |
| 8.0 mm | 5/16 in. | 0.312 | 2.07 |
| 6.7 mm | 0.267 in. | 0.265 | 1.87 |
| 6.3 mm[b] | ¼ in.[b] | 0.250 | 1.82 |
| 5.6 mm | No. 3½ | 0.223 | 1.68 |
| 4.75 mm | No. 4 | 0.187 | 1.54 |

TABLE 1-continued
Nominal Dimensions of Standard Test Sieves
(U.S.A. Standard Series)

| Sieve Designation | | Nominal | Nominal |
|---|---|---|---|
| International Standard[a] (ISO) | U.S.A. Standard | Sieve Opening inches | Wire Diameter mm |
| 4.00 mm | No. 5 | 0.157 | 1.37 |
| 3.35 mm | No. 6 | 0.132 | 1.23 |
| 2.80 mm | No. 7 | 0.111 | 1.10 |
| 2.38 mm | No. 8 | 0.0937 | 1.00 |
| 2.00 mm | No. 10 | 0.0787 | 0.900 |
| 1.70 mm | No. 12 | 0.0661 | 0.810 |
| 1.40 mm | No. 14 | 0.0555 | 0.725 |
| 1.18 mm | No. 16 | 0.0469 | 0.650 |
| 1.00 mm | No. 18 | 0.0394 | 0.580 |
| 850 $\mu m$[c] | No. 20 | 0.0331 | 0.510 |
| 710 $\mu m$ | No. 25 | 0.0278 | 0.450 |
| 600 $\mu m$ | No. 30 | 0.0234 | 0.390 |
| 500 $\mu m$ | No. 35 | 0.0197 | 0.340 |
| 425 $\mu m$ | No. 40 | 0.0165 | 0.290 |
| 355 $\mu m$ | No. 45 | 0.0139 | 0.247 |
| 300 $\mu m$ | No. 50 | 0.0117 | 0.215 |
| 250 $\mu m$ | No. 60 | 0.0098 | 0.180 |
| 212 $\mu m$ | No. 70 | 0.0083 | 0.152 |
| 180 $\mu m$ | No. 80 | 0.0070 | 0.131 |
| 150 $\mu m$ | No. 100 | 0.0059 | 0.110 |
| 125 $\mu m$ | No. 120 | 0.0049 | 0.091 |
| 106 $\mu m$ | No. 140 | 0.0041 | 0.076 |
| 90 $\mu m$ | No. 170 | 0.0035 | 0.064 |
| 75 $\mu m$ | No. 200 | 0.0029 | 0.053 |
| 63 $\mu m$ | No. 230 | 0.0025 | 0.044 |
| 53 $\mu m$ | No. 270 | 0.0021 | 0.037 |

[a]These standard designations correspond to the values for test sieve apertures recommended by the International Organization for Standardization, Geneva, Switzerland.
[b]These sieves are not in the standard series but they have been included because they are in common usage.
[c]1000 $\mu m$ = 1 mm.

For the studies described herein, however, a plurality of the following sieves was used.

| SIEVE # | OPENING SIZE |
|---|---|
| 5 | 4.00 mm |
| 16 | 1.18 mm |
| 30 | 600 um |
| 50 | 300 um |
| 100 | 150 um |
| 230 | 63 um |
| 400 | 38 um |

Upon stacking of the sieves with the largest opening at the top and the finest at the bottom, $LN_2$ is poured over the top sieve to cool the whole system down to $LN_2$ temperature. At this time, an appropriate amount of cryoground tissue powder is placed in the top sieve and the entire stack is subjected to a uniform vibrating process (shaker) for a few minutes. It is important that the tissue powder be kept at or below the brittle temperature, by occasional addition of $LN_2$ throughout the cryosieving process.

Upon completion of cryosieving, "uniform" and "homogeneous" tissue powder is recovered from the top of each individual sieve and can be individually or in a desired combination of particle sizes. Oversize particles can be recycled for further cryogrinding. Distribution of particle size can be obtained from weighing of material on each sieve.

The uniform tissue powder can be further processed, transferred, or stored at regular freezing temperature (e.g., $-18°$ C.=0° F.). However, even at regular freezing temperature some chemical changes (e.g., oxidation of unsaturated lipids, especially because of tremendous surface area generated by cryogrinding; insolubilization or destabilization of proteins; and degradation of pigments and vitamins and other biomolecules) may slowly occur. Reduction of freezer temperature will cause decline of the rates of the above reactions. Consequently, for longer storage times, it is recommended that the final tissue powder be stored at $-40°$ C., under vacuum or inert gas, and in the dark, (to prevent any possible photo-catalytic reactions). Preliminary evaluation shows that various tissue powders stored under the above conditions for up to 2 months, did not show any physical changes (texture, color, odor, etc.) in the product.

To use the uniform cryoground product, one should desirably "thaw" the tissue powder. Since thawing of non-fluid tissues is inherently slower than freezing, when comparable temperature differentials are employed (due to different thermal properties of ice vs. water). Hence, tissue powders may be subject to damage by chemical or physical (and less microbial or enzymatic) means. In light of these considerations, one skilled in the art will recognize that the thawing process must be carefully considered.

III. Advantages of Cryogrinding and Cryosieving

1. The process is straight forward, non-complicated, effective, fast, and clean with minimum loss. Since no medium is added for homogenization, there is no need for an extra step (e.g., centrifugation) for removal of any medium. The process is technology adaptable.

2. Due to physical treatment at extremely low temperature, there are no adverse effects or hazards for microbial or enzymatic activity or other undesirable thermally-catalyzed chemical reactions. Consequently, while tissues are "physically" powdered, their "biochemical and chemical" integrity is preserved. The process is compatible with biomolcules 3. Since the resultant cryoground and cryosieved tissues are free-flowing powders, their handling (e.g., weighing, transferring, mixing, pouring, etc.) in laboratory and/or plant is very easy.

4. The resultant tissue powders, due to their extreme homogeniety, may be used as reliable common sources for comparative analytical and preparative research and development studies.

5. Preparation of cosmetic, pharmaceutical, and food products by combination of cryogrinding and cryosieving as a safe tissue homogenization method and aqueous or SCF extraction and/or mild thermal treatment as safe extraction methods will be very acceptable to health authorities. The impact on consumer acceptance and marketability are obviously enormous.

6. Since the process brings about tremendous increases in the surface area to volume ratio, it will cause higher recovery or yield in the follow-up separation processes. Consquently this process effectively reduces the overall processing cost (time, chemical, energy, and resources) and therefore is economically feasible.

EXAMPLE 1

Following the general protocol explained supra cryogrinding was applied to porcine omentum and a pinkish "omentum powder" was obtained. Upon cryosieving, the best uniform fraction of omentum powder appeared to be in the range of 150 to 600 $\mu m$.

EXAMPLE 2

Following the general protocol explained supra cryogrinding was applied to porcine brain and a white "brain powder" was obtained. Upon cryosieving, the best uniform fraction of brain powder appeared to be in the range of 300 μm to 1.18 mm.

EXAMPLE 3

Following the general protocol explained supra cryogrinding was applied to porcine pancreas and a white "pancreas powder" was obtained. Upon cryosieving, the best uniform fraction of pancreas powder appeared to be in the range of 150 μm to 1.18 mm.

EXAMPLE 4

Following the general protocol explained supra cryogrinding was applied to porcine spinal chord and a white "spinal chord powder" was obtained. Upon cryosieving, the best uniform fraction of spinal chord powder appeared to be in the range of 150 μm to 600 μm.

EXAMPLE 5

Following the general protocol explained supra cryogrinding was applied to porcine liver and a "liver powder" was obtained. Upon cryosieving, the best uniform fraction of liver powder appeared to be in the range of 300 μm to 1.18 mm.

EXAMPLE 6

Following the general protocol explained supra cryogrinding was applied to porcine kidney and a "kidney powder" was obtained. Upon cryosieving, the best uniform fraction of kidney powder appeared to be in the range of 300 μm to 1.18 mm.

EXAMPLE 7

Following the general protocol explained supra cryogrinding was applied to porcine spleen and a "spleen powder" was obtained. Upon cryosieving, the best uniform fraction of spleen powder appeared to be in the range of 300 μm to 1.18 mm.

EXAMPLE 8

Following the general protocol explained supra cryogrinding was applied to porcine blood and a "blood powder" was obtained. Upon cryosieving, the best uniform fraction of blood powder appeared to be in the range of 150 to 300 μm.

EXAMPLE 9

Following the general protocol explained supra cryogrinding was applied to porcine Subcutaneous Adipose Tissue (PSAT) and a "PSAT powder" was obtained. Upon cryosieving, the best uniform fraction of PSAT powder appeared to be in the range of 150 μm to 1.18 mm.

EXAMPLES 10 TO 26

The general protocol explained supra, is used to prepare "powder" from all animal tissues, organs, and cells, for example, central nervous system tissues and organs (brain, spinal chord, spinal fluid, appendages); peripheral nervous system tissues and organs (cranial nerves, spinal nerves, etc.); mycardial and vascular tissues and organs (heart, arteries, and veins); circulatory tissues and organs (blood, erythrocytes, leukocytes, platelets, plasma); lymphatic system tissues and organs (lymph nodes, spleen, thymus); respiratory system tissues and organs (upper respiratory tract, lungs); digestive system tissues and organs (including mouth, teeth, tongue, salivary glands, pharynx, esophagus, peritoneum, stomach, small and large intestine, liver, gall bladder, pancreas); skeletal tissue and organs (axial and appendicular skeleton, bone marrow); muscles (smooth and skeletal); endothelial and epithelial tissue; membranes, omentum, and cartiligenous tissues (tendons, ligaments, joints); sensory organs (eyes, ear, nose, tongue); endocrine or other glandular tissue (thyroid gland, parathyroid gland, pituitary gland, adrenal gland); urinary tissue and organs (kidneys, ureters, urinary bladder, urethra); reproductive organs and tissues (testes, ovaries, etc.); and adipose tissues such as is contained in subcutaneous and internal organs, as well as biological exudates, such as feces, urine, sweat, semen, milk, and so forth, are used. In each case such processing conditions are chosen which optimizes the physical and rheological characteristics of the desired powder.

EXAMPLE 27

Chloroform/Methanol Extraction of Omentum Powder 500 g. uniform porcine omentum powder was warmed up to room temperature and extracted with 10 times chloroform/methanol (2:1, v/v) in a glass blender (22,000 RPM, 30 seconds). The solvent extract was centrifuged (2,000 RPM, 20 minutes) and subjected to rotary evaporation (under vacuum, 37° C.) until dryness, i.e., neither any solvent condensation occurs, nor any solvent odor is present. A whitish chloroform/methanol fraction (CMFr) weighing 388 g. (i.e., 77.6%) was obtained. The CMFr could be further subjected to a hexane/ethanol fractionation.

EXAMPLE 28

Direct Hexane Extraction of Omentum Powder 500 g. uniform procine omentum powder was warmed up to room temperature and extracted with 10 times hexane in a glass blender (22,000 RPM, 30 seconds). The resultant pinkish solution was centrifuged at 2000 RPM for 20 minutes. If centrifugation is performed at room temperature, only a pinkish solid layer precipitates as pellet. However, if centrifugation is done at refrigerated temperature (e.g., 5° C.), where solubility powder of hexane is reduced, a white layer of lipids will also precipitate on top of the proteinacious pinkish pellet. This layer, however, will easily go into solution if the hexane is warmed up to room temperature or, preferably, to 37° C. Hexane extract was subjected to rotary evaporation under vacuum and at 37° C. Total recovery of direct hexane extraction of porcine omentum powder was 361.5 g. (i.e., 72.3%).

EXAMPLE 29

Supercritical $CO_2$ Extraction of Omentum Powder 1905.4 g. uniform porcine omentum powder was extracted with $SC$-$CO_2$ in four trial batches. The solvent to feed ratio of 300 (1 lb./min.) was used. A total of 12 extract fractions were collected from each run. The extractor was maintained at 37° C. and 3500 psig, first separator at 40° C. and 1500 psig, and second separator at 29°–30° C. and about 1000 psig, where the bulk of extract was collected. The solvent from the second separator was fed into a knock-out vessel at about 1500 psig and then recycled. The residue in the extractor was in the range of 8–17% of the feed. It was interesting to find out that SC-CO$_2$ extracts about 83–92% of the feed which is more than chloroform/methanol (with traditional homogenization practice). This would suggest that cryogrinding prior to extraction is indeed effective.

EXAMPLE 30

Mild Thermal Extraction of Omentum Powder

In order to thermally extract lipids from omentum or any other fatty tissue, it is necessary to: (1) melt or liquefy lipids, (2) separate melted lipids from the rest of the tissue, and (3) filter the resultant oil or fat from residues. All above steps were combined as "one step" as follows:

1000 g. uniform porcine omentum powder was placed in two stainless steel 150 um (#100) sieves. These sieves were stacked on the top of 38 um (#400) sieves and collecting pans. The stacks were placed in an oven with mild heat (70° C.). Upon gradual thawing of omentum powder, lipids became gradually melted while proteinaceous materials became denatured. This resulted in the shrinkage and final collapse of the powdery structure of omentum powder. Melted lipid, however, easily passes through a 150 um sieve and fell as droplets on the 38 $\mu$m sieve, where it was filtered and separated from small residue particles, and finally clear oil was collected in the collecting pans. The total thermal extraction time was 3 hours, during which occasional mixing occurred. Total recovery was found to be 709.5 g. (i.e., 73.6%). It is notable that above recovery does not cover the compression of the remaining oily materials on the top sieve.

Considering examples 27 to 30, it is interesting to find out that when omentum "powder" (rather than traditional cell breaking method) is used, not only processing and handling of the raw material is much easier for all types of follow-up extractions, but the percent lipid recovery of all above examples are higher than the traditional method of cell breaking (i.e., via PBS). Better quality and higher recovery obviously gives a great appeal to cryogrinding and cryosieving for tissue processing.

EXAMPLE 31

100 g. uniform porcine brain powder was extracted with chloroform/methanol similar to Example 27. Near the end of the evaporation, foaming occurred (possibly due to high concentration of phospholipids), so evaporation was continued with partial vacuum and at a reduced rate. Brain CMFr could be removed physically from evaporating flask or taken out by water which then could be removed by freeze drying. The total CMFr recovery was 7.3 g. (i.e., 7.3%)

EXAMPLE 32

31.2 g. uniform porcine pancreas powder was extracted with chloroform/methanol similar to Example 27. The total CMFr recovery was 3.8 g. (i.e., 12.2%).

EXAMPLE 33

79.7 g. uniform porcine spinal chord powder was extracted with chloroform/methanol similar to Example 27. The total CMFr recovery was 8.5 g. (i.e., 10.7%).

EXAMPLE 34

100 g. uniform porcine liver powder was extracted with chloroform/methanol similar to Example 27. Upon centrifugation, particles were still suspended in the supernatant. They were removed by glass wool filter and a clear yellowish solution was obtained. The total CMFr recovery was 8.7 g. (i.e., 8.7%).

EXAMPLE 35

100 g. uniform porcine kidney powder was extracted with chloroform/methanol similar to Example 34. The total CMFr recovery was 9.5 g. (i.e., 9.5%).

EXAMPLE 36

100 g. uniform porcine spleen powder was extracted with chloroform/methanol similar to Example 27. The total recovery was 9.0 g. (i.e., 9.0%).

EXAMPLE 37

400 g. uniform porcine blood powder was extracted with chloroform/methanol similar to Example 34 but with 2 time filtration. The total recovery was 3.8 g. (i.e., 0.95%).

EXAMPLE 38

500 g. uniform porcine subcutaneous adipose tissue (PSAT) powder was directly extracted with hexane similar to Example 28. The total recovery was 414.6 g. (i.e., 82.9%).

EXAMPLE 39

To obtain various classes of omentum lipids as a function of temperature, 300 g. uniform porcine omentum powder was placed in a stack of sieves as described in Example 30. The stack with cold omentum powder ($-40°$) was placed in a 40° C. oven for 20 hours and oil in the collecting pan was recovered. After this initial step, the oven temperature was increased by 10° C. increments. The coming-up time for each 10° increment was ten minutes, while samples were heated as desirable temperature for one and one-half hours. The recovery of fractions were as follows:

| Oven Temperature (°C.) | % Recovery |
|---|---|
| 40 | 1.1 |
| 50 | 30.6 |
| 60 | 22.4 |
| 70 | 4.8 |
| 80 | 6.7 |
| Residue (top sieve) | 12.5 |
| Loss (including water) | 21.9 |

It is clear that the most lipids are recovered at the oven temperature of 50° C.

EXAMPLE 40

To apply the fundamental understanding of Brittleness Temperature and cryogrinding to plant tissues, we followed the general protocol explained supra, by grinding two 700 g. unhulled soybean samples at Room Temperature (R.T.) as well as LN$_2$ Temperature, i.e., cryogrinding for two minutes. The resultant "soy flour" were subjected to cryosieving for five minutes at LN$_2$ temperature. The percent distribution of particle size was calculated from weighing the materials on each sieve:

| Particle size> | R.T. Grinding | Cryogrinding |
|---|---|---|
| 1.18 $\mu$m | 17.30 | 5.90 |

-continued

| Particle size> | R.T. Grinding | Cryogrinding |
|---|---|---|
| 600 μm | 39.10 | 40.80 |
| 300 μm | 37.90 | 45.60 |
| 150 μm | 4.60 | 6.80 |
| 63 μm | 0.93 | 0.69 |
| Collecting Pan | 0.27 | 0.13 |

It is clear that cryogrinding causes production of particles with smaller sizes. This may improve the oil recovery, when compared to equally treated, but flaked or R.T. ground soy flour. 250 g. of the resultant cryoground soy flour (from 600 μm sieve) was extracted with 15 times hexane at room temperature. The resultant cloudy solution was centrifuged at 2000 RPM for 20 minutes. Upon centrifugation, the clear yellowish supernatant was rotary evaporated at 37° C. under vacuum. Total recovery was 24.3 g. (i.e., 9.7%).

One skilled in the art will recognize the applicability of the method described herein to any and all extraction processes. Cryogenic treatment of tissue followed by cryogrinding of the thus treated tissue, privides one with materials with very small particle size and enormous surface area in a form suitable for obtaining improved quantities and qualities of desired extracts.

The materials which can be extracted using the processes described herein include, but are not limited to, complex lipids, such as acylglycerols, phosphoglycerides, sphingolipids, gangliosides and waxes; simple lipids, such as terpenes, pigments, steroids, and their alcohols (sterols), prostaglandins, and so forth. Glycolipids, lipoproteins, membrane supramolecular complexes, and their metabolic intermediates, be they catabolic or anabolic, and metabolic products of these molecules, as well as molecules which behave in a fashion similar to lipids, may be obtained in a fashion similar to that given in the examples, supra. Polar, non-polar and amphipathic biomolecules may be obtained as well.

Additional molecules may be obtained by the processes of this invention as well. For example "proteinaceous" substances, such as amino acid containing substances (including non-protein amino acids), oligopeptides, peptides, polypeptides, hormones, proteins, enzymes, antibodies, fractions and components of these, as well as metabolic intermediaries and products may be obtained. While the choice of temperatures, solvents, SCFs and reaction parameters will vary, depending upon the substance to be extracted, one skilled in the art will be able to determine which reagents and conditions to use. Typical examples of solvents include aqueous, and organic solvents including but not being limited to, phosphate buffered saline (PBS); hexane; dimethyl sulfoxide (DMSO); methanol; acetic acid; ethanol; acetonitrile; chloroform; propylene glycol, propanol; and ethyl ether. Either a single solvent or a plurality of solvents may be used.

Saccharides, including mono-, di-, oligo- and polysaccharides, as well as glycoproteins may be extracted in this way as well. Again, metabolic intermediates and products can be obtained as well.

The nucleotide family of molecules, including purines and pyrimidines, and any molecules containing nucleic acid bases, nucleosides (ribonucleosides and deoxyribonucleosides), nucleic acids, supramolecular complexes of nucleic acids and proteins, viruses, and so forth as well as their intermediates and products, metaolic products may also be obtained.

In addition, materials not grouped into one of the "families" listed supra, may be obtained. These include all fat and/or water soluble vitamins, flavors, flavor potentiators, their intermediates, both catabolic and anabolic, and products as well.

It is not to be assumed that the method can be used only to obtain desired products. Undesirable substances, such as toxins, allergens, and so forth, may be removed from a sample, following this invention. Hence, one skilled in the art will note that this method has application for biological purification processes, where it is necessary to remove undesirable substances.

In cryogrinding and cryosieving treatments of animal derived materials, the desired material may also be treated with one or any combination of more than one of the following methods of treating the samples:

1. Physical treatments; including crushing, comminuting, high and low pressure pressing, flaking, sonication, freeze-thaw treatment, emulsification, homogenization, filtration, high speed mixing, centrifugation, mechanical separation and thermal treatments including microwave treatment.
2. Chemical treatments; including treatments with inorganic and organic acids, bases, solvents, surface active agents, colorants, and ionizing radiation.
3. Enzymatic treatments; including endogenous and/or exogenous enzymatic treatments.

The samples need not be treated prior to cryogrinding, but may, e.g., be treated after the preparation of tissue powder.

Supercritical fluid extraction may be accomplished with many different gases, including those listed in the following Table II.

TABLE II

| | SYMBOL | CRITICAL TEMP. (°C.) | CRITICAL PRESSURE (atm.) |
|---|---|---|---|
| (A) ELEMENTALS | | | |
| (a) Noble gases: | | | |
| (1) Helium | He | −267.9 | 2.26 |
| (2) Neon | Ne | −228.7 | 27.9 |
| (3) Argon | Ar | −122.3 | 48.0 |
| (4) Krypton | Kr | −63.8 | 54.3 |
| (5) Xenon | Xe | 16.6 | 58.0 |
| (b) Others: | | | |
| (6) Nitrogen | $N_2$ | −147.0 | 33.5 |
| (7) Hydrogen | $H_2$ | −239.9 | 12.8 |
| (8) Oxygen | $O_2$ | −118.4 | 50.1 |
| (9) Ozone | $O_3$ | 12.0 | 55.0 |
| (10) Fluorine | $F_2$ | −129 | 55 |
| (B) INORGANIC COMPOUNDS | | | |

TABLE II-continued

|  | SYMBOL | CRITICAL TEMP. (°C.) | CRITICAL PRESSURE (atm.) |
|---|---|---|---|
| (examples) | | | |
| (1) Ammonia | $NH_3$ | 132.5 | 112.5 |
| (2) Boron Trifluoride | $BF_3$ | −12.26 | 49.2 |
| (3) Carbon Dioxide | $CO_2$ | 31.0 | 72.9 |
| (4) Carbon Monoxide | CO | −140 | 34.5 |
| (5) Hydrogen Chloride | HCl | 51.4 | 82.1 |
| (6) Hydrogen Sulfide | $H_2S$ | 100.4 | 88.9 |
| (7) Nitric Oxide | NO | −93 | 64 |
| (8) Nitrogen Dioxide | $NO_2$ | 157.8 | 100 |
| (9) Nitrous Oxide | $N_2O$ | 36.5 | 71.7 |
| (10) Silane | $SiH_4$ | −3.46 | 47.8 |
| (11) Silane Chlorotrifluoro | $SiClF_3$ | 34.5 | 34.5 |
| (12) Silicon Tetra Fluoride | $SiF_4$ | −14 | 36.7 |
| (13) Sulfur Dioxide | $SO_2$ | 157.8 | 77.7 |
| (14) Sulfur Hexafluoride | $SF_6$ | 45.6 | 37.1 |
| (15) Water | $H_2O$ | 374.1 | 218.3 |
| (C) ORGANIC COMPOUNDS (examples) | | | |
| (a) Alkanes: | | | |
| 1. Methane | $CH_4$ | −82.1 | 45.8 |
| 2. Ethane | $C_2H_6$ | 32.2 | 48.2 |
| (3) Propane | $C_3H_8$ | 96.8 | 42 |
| (4) n-butane | $C_4H_{10}$ | 152 | 37.5 |
| (5) iso-butane | $C_4H_{10}$ | 134.7 | 35.9 |
| (b) Alkenes: | | | |
| 6. Ethene (Ethylene) | $C_2H_4$ | 9.9 | 50.5 |
| 7. Propene (Propylene) | $C_3H_6$ | 91.9 | 44.4 |
| 8. n-butene | $C_2H_8$ | 1546 | 39.7 |
| (c) Alkynes: | | | |
| 9. Ethyne (acetylene) | $C_2H_2$ | 35.5 | 61.6 |
| (d) Alkyhalides: | | | |
| 10. Monofluoro Methane | $CH_3F$ | 44.6 | 58 |
| 11. Trifluoro Methane (Fluoroform) | $CHF_3$ | 25.9 | 46.9 |
| 12. Tetrafluoro Methane | $CF_4$ | −45.7 | 41.4 |
| 13. Monochlorodifluoro Methane | $CHClF_2$ | 96 | 48.5 |
| 14. Monochlorotrifluoro Methane | $CClF_3$ | 28.8 | 38.2 |
| 15. Dichlorodifluoro Methane | $CCl_2F_2$ | 111.5 | 39.6 |
| 16. Monobromotrifluoro Methane | $CBrF_3$ | 67 | 50.3 |
| 17. Monofluoro Ethane | $C_2H_5F$ | 102.2 | 49.6 |
| 18 Hexafluoro Ethane | $C_2F_6$ | 24.3 | — |
| 19. Chloropenatfluoro Ethane | $C_2ClF_5$ | 80 | — |
| 20. Perfluoro butane | $C_4F_{10}$ | 113.2 | 23 |
| 21. 1,1-difluro Ethylene | $C_2H_2F_2$ | 30.1 | — |

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. Method for obtaining a desired substance from animal material comprising freezing said animal material to its Brittleness Temperature with liquified inert gas, cryogrinding said material into a cryopowder, wherein the temperature at which grinding takes place is or is maintained at no higher than said Brittleness Temperature, and extracting said substance from said cryopowdered animal material by means of a process selected from the group consisting of aqueous solvent extraction, organic solvent extraction, supercritical extraction and thermal extraction.

2. Method of claim 1, wherein said material is a tissue.

3. Method of claim 2, wherein said tissue is selected from the group consisting of muscle, cartiligenous, vascular, circulatory, lymphatic, respiratory, skeletal, sensory, urinary, and reproductive tissue.

4. Method of claim 2, wherein said tissue is adipose tissue.

5. Method of claim 2, wherein said tissue is nerve tissue.

6. Method of claim 2, wherein said tissue is endothelial tissue.

7. Method of claim 2, wherein said tissue is epithelial tissue.

8. Method of claim 2, wherein said tissue is myocardial tissue.

9. Method of claim 2, wherein said tissue is glandular tissue.

10. Method of claim 2, wherein said tissue is digestive tissue.

11. Method of claim 1, wherein said material is an organ.

12. Method of claim 11, wherein said organ is the omentum.

13. Method of claim 11, wherein said organ is the brain.

14. Method of claim 1, wherein said liquified inert gas is liquid nitrogen.

15. Method of claim 1, wherein said material is frozen by immersing said material in a liquid form of said inert gas.

16. Method of claim 1, wherein said extracting comprises extraction with an aqueous solvent.

17. Method of claim 1, wherein said extracting comprises extraction with a buffer.

18. Method of claim 1, wherein said extracting comprises extraction with hexane.

19. Method of claim 1, wherein said extracting comprises extraction with a compound selected from the group consisting of methanol, ethanol, propanol, propylene glycol and ethylether.

20. Method of claim 1, wherein said extracting comprises extraction with supercritical $CO_2$.

21. Method of claim 1, wherein said desired substance is a lipid containing molecule.

22. Method of claim 1, wherein said desired substance is an amino acid containing molecule.

* * * * *

UNITED STATES PATENT AND TRADEMARK OFFICE
CERTIFICATE OF CORRECTION

PATENT NO. : 4,776,173

DATED : October 11, 1988

INVENTOR(S) : Ahmad R. Kamarei, et al.

It is certified that error appears in the above-identified patent and that said Letters Patent is hereby corrected as shown below:

Column 2, line 6: change "filter" to -- filler --.

Column 4, line 67: change "0.267" to -- 0.265 --.

Column 8, line 48: change "powder" to -- power --.

Column 13, line 15: change the second "34.5" to -- 34.2 --.

Column 13, line 27: change "44.4" to -- 45.5 --.

Column 13, line 28: change "$C_2H_8$" to -- $C_4H_8$ --, change "1546" to -- 146 --.

Signed and Sealed this

Twentieth Day of June, 1989

Attest:

DONALD J. QUIGG

*Attesting Officer*  *Commissioner of Patents and Trademarks*